United States Patent [19]

Rycheck et al.

[11] 4,101,592

[45] Jul. 18, 1978

[54] CATALYTIC HYDROGENATION

[75] Inventors: Mark R. Rycheck; Filippo Pennella, both of Bartlesville, Okla.

[73] Assignee: Phillips Petroleum Company, Bartlesville, Okla.

[21] Appl. No.: 765,515

[22] Filed: Feb. 4, 1977

[51] Int. Cl.$^2$ .......................... C07C 13/00; C07C 5/02
[52] U.S. Cl. .............................. 260/666 P; 260/683.9; 204/284; 260/666 R
[58] Field of Search ............. 260/683.9, 666 P, 666 R; 204/284

[56]  References Cited

U.S. PATENT DOCUMENTS

| | | | |
|---|---|---|---|
| 2,428,692 | 10/1947 | Voorhies | 260/683.6 |
| 3,379,635 | 4/1968 | von Doehren et al. | 204/284 |
| 3,666,412 | 5/1972 | Sowards | 23/162 |

OTHER PUBLICATIONS

Comprehensive Inorganic Chemistry vol. 1, pp. 724–728, 1210–1213, 1359, J. C. Bailar et al. Editors, Pergamon Press, Oxford, England 1973.
Comprehensive Inorganic Chemistry vol. 2, pp. 228–229, 234, 238; J. C. Bailar et al. Editors, Pergamon Press, Oxford, England 1973.
H. Remy Treatise on Inorganic Chemistry, vol. 1, pp. 467, 474, 619, Elsevier Press, 1956.

Primary Examiner—Veronica O'Keefe

[57]  ABSTRACT

Monoolefins are hydrogenated in the presence of a catalyst comprising at least one carbide, nitride, or silicide of a Group VIII, Group VIB, or Group VIIB metal.

10 Claims, No Drawings

CATALYTIC HYDROGENATION

BACKGROUND OF THE INVENTION

This invention relates to a catalytic hydrogenation process. In particular, it relates to catalytic hydrogenation of monoolefins.

At normal temperatures and pressures, hydrogen does not react with olefins; however, when a suitable catalyst is provided, hydrogen adds to a double bond of a monoolefin forming a corresponding paraffin. Finely divided platinum, palladium, Raney nickel, and metal borides (as disclosed in U.S. Pat. No. 3,379,635) were found to be useful catalysts in the hydrogenation process. In view of the commercial importance of the process, the search for a catalyst which allows hydrogenation, and especially one that allows hydrogenation at moderate temperatures and pressures, continues.

The present invention contributes to the art of catalytic hydrogenation of monoolefins by providing a hydrogenation process which utilizes a novel catalyst.

Thus, one object of the present invention is to provide an improved catalytic hydrogenation process.

Another object of the invention is to provide a catalyst which enables hydrogenation of monoolefinic hydrocarbons at moderate temperatures and pressures.

A further object of the invention is to provide a hydrogenation process which utilizes commercially available catalysts.

Other objects of the invention will become apparent to those skilled in the art upon studying this disclosure.

SUMMARY OF THE INVENTION

Monoolefinically unsaturated hydrocarbons are hydrogenated at moderate temperatures in the presence of a catalyst comprising at least one carbide, nitride, or silicide, of a Group VIII, Group VIB, or Group VIIB metal.

Other aspects of the invention will become apparent to those skilled in the art upon studying this disclosure.

DETAILED DESCRIPTION OF THE INVENTION

It has been discovered that hydrogenation of monoolefinically unsaturated hydrocarbons can be accomplished at moderate temperatures under reaction conditions by contacting the reagents in the presence of a catalyst which comprises a carbide, nitride, or silicide of a Group VIII, Group VIB, or Group VIIB metal (as depicted in *Hackh's Chemical Dictionary*, McGraw-Hill Book Company, 4th Edition, page 415). The term Group VIII metal throughout this disclosure shall include: Fe, Co, Ni, Ru, Rh, Pd, Os, Ir, and Pt. Among preferred metals are molybdenum, tungsten, manganese, iron, cobalt, and nickel. Illustrative compounds include FeC, MnC, $Mo_2C$, $Co_2C$, $Ni_3C$, MoN, $MoSi_2$, WC, and $W_2C$ and mixtures thereof. The presently preferred catalysts include: FeC, MnC, $Mn_2C$, MoN, $MoSi_2$ and a mixture of 50 weight percent of WC and 50 weight percent of $W_2C$. Especially preferred because of superior conversions are $Mo_2C$ and 50/50 weight mixture of WC and $W_2C$.

Generally the catalysts of this invention are either commercially available compounds or produced in accordance with known methods. In general, the carbides can be prepared by heating the metal with carbon; the nitrides can be prepared by heating the metal or metal oxide with nitrogen or ammonia, or by heating the metal amide, and; the silicides can be prepared by heating the metal with silicon or silica. The preparation of the compounds are briefly described in Volume 1 of Remy, "Treatise on Inorganic Chemistry", pages 467, 619, and 474, respectively. The catalysts thus produced, are crystalline powders having high melting points generally above about 815° C (1500° F) and relatively low surface areas (about $0.5-10 m^2/g$). Prior to the use in the hydrogenation reaction, the catalysts are activated by heating these in a hydrogen atmosphere. The activation temperature and time varies with the type of the catalyst used. Although adequate activation can be achieved over a wide temperature range in most applications, the activation temperatures for the hydrogenation catalysts of this invention range from about 300° C to about 600° C (572° F – 1112° F), preferably from about 500° C to about 600° C (932° F – 1112° F) and the activation time is about one to three hours.

The hydrogenation reaction can be conducted using the catalysts of this invention either in a batch, or in a continuous manner. The minimum reaction conditions, including temperature and pressure maintained in a reaction zone, are such as to allow conversion of at least some of the monoolefins to corresponding paraffins. The maximum temperature level is below the decomposition temperature of the hydrocarbons present in the reaction zone (at the pressure maintained in the reaction zone). The preferred temperature in the reaction zone can vary depending on the type of the catalyst, the type of reagents, and other reaction conditions, from about 100° to about 450° C (212° F – 842° F). The reaction pressure is generally between atmospheric pressure, i.e., 14.7 psi (101 kPa gage), about 500 psi (3450 kPa gage). The mole ratio of olefin to hydrogen can vary from about 1:1 to about 1:20, preferably from about 1:2 to about 1:15.

In a continuous gas phase process, the space velocity of hydrocarbon can vary from about 1 to about 500 volumes feed per volume catalyst per hour (GHSV). In a batch process, the contact time between the reagents and the catalyst usually ranges from about 10 minutes to about 20 hours.

The olefins that can be hydrogenated in accordance with the process of this invention are linear, branched, and cyclic monoolefins containing from 2-20 or more carbon atoms per molecule. Representatives of these are ethylene, propylene, 1-butene, cis-2-butene, trans-2-butene, 1-pentene, 3-methyl-1-butene, 1-hexene, 2,3-dimethyl-1-butene, 2-methyl-2-pentene, 1-heptene, 1-octene, 1-dodecene, 1-eicosene, cycloheptene, cyclohexene, and mixtures thereof. Presently preferred compounds as feeds for the hydrogenations are acyclic monoolefins containing from 2 to about 12 carbon atoms per molecule. The catalysts of this invention are especially useful in hydrogenation of butene-2 to butane.

In operation, the catalyst, usually in powder form, is placed on a suitable support in a reactor and heated in the presence of hydrogen to a temperature about equal to the maximum hydrogenation temperature to be employed or from about 260° C (500° F) higher than that temperature for a period of time sufficient to activate it. Then the temperature of the reactor and the catalyst is adjusted to the level at which hydrogenation is to be conducted, and hydrogen, together with olefinically unsaturated hydrocarbons, is introduced into the reactor. The contact time is adjusted to allow desired conversion of monoolefins to paraffins. The contacting of the reagents in the presence of the catalyst can be carried out, either in a batch, or in a continuous manner.

The effluent from the reactor is removed and separated into unreacted hydrogen, unreacted olefins, if present, and paraffins by a suitable method such as fractional distillation. The hydrogen and monoolefin streams, separated from the effluent stream, can be recycled to the reaction zone as desired and the paraffin stream is recovered as product.

Many variations and modifications of this invention will become apparent to one skilled in the art upon studying this disclosure. For example, although the catalyst was described in connection with the process for hydrogenation of olefins, it is believed that it would be also suitable for hydrogenation of acetylenic compounds to form paraffins. All changes that are within the spirit of this invention are intended to be included within its scope.

The following example is provided for illustrative purposes and is not intended to limit the invention in any manner.

EXAMPLE

A series of separate hydrogenation runs was made using commercially purchased powders of metal carbides, nitrides, and silicides shown in the Table. The runs were conducted in a tubular glass reactor having a glass wool plug as a catalyst support in accordance with the following procedure.

In each run, a 3 mm deep layer of silica particles, having mesh size of about 20–40 (U.S. Sieve Series), was placed on the glass wool plug and the catalyst was placed on the top of the silica layer. A thermocouple was then inserted into the center of the catalyst bed to measure the reaction temperature. The reactor and its contents were then heated to the catalyst activation temperatures (shown in the Table), and hydrogen was continuously passed through the catalyst bed for periods of time indicated in the Table. After activation of the catalyst, the reactor and its contents were cooled to about 30° – 50° C (86° –122° F) as hydrogen was allowed to flow through the reactor. Butene-2 was then metered into the hydrogen stream (the respective flow rates are shown in the Table) and the temperature, in the reactor, was increased in 50° C (122° F) steps until it reached 450° C (842° F). The temperature was then decreased in a stepwise manner until it reached 150° C (302° F). At each temperature level, the effluent from the reactor was analyzed by means of gas-liquid chromatography in a column containing bis[2-(2-methoxyethoxy)-ethyl]ether, and the weight percentages of butene-2 converted into n-butane was calculated. The activation condition, feed rates, and the result for each run, are presented in the Table. The surface area of each catalyst shown in the Table was determined prior to the activation.

TABLE

| Run No. | 1 | 2 | 3 | 4 | 5 | 6 | 7 | 8 | 9 |
|---|---|---|---|---|---|---|---|---|---|
| Catalyst | | | | | Hydrogenation of Butene-2 | | | | |
| Description | FeC | MnC | Mo$_2$C | WC$^{(1)}$ | WC$^{(1)}$ | MoN | MoN | MoSi$_2$ | MoSi$_2$ |
| Activation Time, Hrs. | 1.0 | 1.0 | 1.0 | 3.0 | 1.0 | 1.5 | 2.0 | 1.5 | 2.0 |
| Activation Temp. °C | 300 | 300 | 300 | 600 | 300 | 300 | 600 | 300 | 600 |
| Surface Area, m$^2$/g | 3.0 | 9.5 | 1.0 | 0.4 | 0.4 | 0.8 | 0.8 | 5.3 | 5.3 |
| Feed Rate, GHSV | | | | | | | | | |
| Butene-2 | 90 | 129 | 90 | 90 | 300 | 90 | 90 | 90 | 90 |
| Hydrogen | 900 | 1290 | 900 | 900 | 3000 | 900 | 900 | 900 | 900 |
| Hydrogenation Temp. °C | | | Weight Percent Butene-2 Converted to n-Butane | | | | | | |
| 100 | 4.9 | 0.20 | 0.21 | na$^{(2)}$ | na$^{(2)}$ | na$^{(2)}$ | 0.61 | 0.50 | 0.90 |
| 150 | 14.0 | 0.60 | 5.0 | 98.6 | 98.7 | 0.17 | 0.33 | 0.60 | 0.27 |
| 200 | 28.4 | 0.30 | 61.7 | 98.7 | 97.3 | 1.5 | 4.2 | 1.0 | 0.19 |
| 250 | 18.1 | 0.30 | 95.2 | 99.0 | 84.0 | 9.8 | 27.2 | 3.4 | 1.7 |
| 300 | 43.9 | 0.30 | 98.2 | 98.6 | 51.2 | 22.1 | 43.5 | 12.6 | 13.2 |
| 350 | 0.40 | 0.50 | 93.9 | 99.7 | 21.0 | 41.7 | 39.6 | 34.2 | 16.5 |
| 400 | 0.56 | 20.4 | 60.5 | 67.8 | 16.0 | na$^{(2)}$ | 22.7 | 25.6 | 12.3 |
| 450 | 0.28 | 5.4 | 23.8 | 37.0 | 5.2 | 10.6 | 10.2 | 6.9 | 6.5 |
| 350 | 0.28 | 1.7 | na$^{(2)}$ | 82.3 | 86.6$^{(300°\,C)}$ | na$^{(2)}$ | 9.4 | 5.7 | 6.0 |
| 250 | na$^{(2)}$ | 0.3 | 28.2 | 98.8 | 99.6$^{(200°\,C)}$ | 1.4 | 2.9 | 1.3 | 1.8 |
| 150 | 0.60 | na$^{(2)}$ | 4.3 | 99.6 | 99.9 | 0.58 | 0.20 | 0.80 | 0.74 |

Notes:
$^{(1)}$X-ray showed a mixture of approximately $\frac{50}{50}$ wt. % WC and W$_2$C.
$^{(2)}$not available.

The results indicate that effective hydrogenation of olefins can be conducted in the temperature range from about 100° – 450° C (212 – 842° F). The temperature allowing best conversion rates varied depending on the activation treatment, feed rates, and the particular catalyst used. The hydrogenation in Run 1, using FeC as catalyst, was most effective at a temperature between 150° and 300° C (302° – 572° F). The best results in the hydrogenation in Run 2, using MnC as catalyst, were achieved at about 400° C (752° F). The best results in Run 3 (Mo$_2$C) were obtained at temperatures between 200° and 400° C (392° – 752° F), whereas with WC/W$_2$C (Run 4), the best results were obtained in the temperature range from about 150° C – 350° C (302° – 662° F). The catalyst in Runs 4 and 5 WC/W$_2$C functions the best at temperatures between 150° C and 350° C (302° – 662° F). The best results in Runs 6 and 7, MoN used as catalyst, were obtained at temperatures between about 250° C to about 350° C (482 – 662° F). MnSi$_2$ catalyst, used in Runs 8 and 9, is most effective at temperatures between 300° – 400° C (572 – 752° F).

The comparison of Runs 4 and 5, in which the same type of catalyst was used, but the catalyst activation temperatures and time, as well as feed rates varied, indicates that a WC/W$_2$C catalyst activated at a higher temperature and for a longer period of time, retains its activity better at relatively high hydrogenation temperatures. A comparison of Runs 6 and 7 suggest that the MoN catalyst, activated at a higher temperature, is more active than that activated at a lower temperature. Finally, the results of Runs 8 and 9 indicate that an MoSi$_2$ catalyst, activated at a higher temperature, performs better than the same catalyst activated at a lower temperature.

We claim:

1. A process for hydrogenation of monoolefins which comprises:

contacting in a reaction zone at least one monoolefinic hydrocarbon with hydrogen in the presence of a catalyst consisting essentially of at least one of carbides, nitrides, and silicides of Group VIII, Group VIB, and Group VIIB metals, at such conditions, including temperature and pressure, and for such period of time as to allow conversion of at least some of the monoolefins to corresponding paraffins, said catalyst having been activated prior to said contacting by heating with hydrogen at an elevated temperature and for a period of time sufficient to activate said catalyst for hydrogenation of monoolefins to paraffins.

2. A process as claimed in claim 1 wherein the contacting is carried out in a batch manner; the temperature in the reaction zone is in the range from about 100° C to about 450° C (212° – 842° F); the pressure is in the range from about 14.7 psi (101 kPa gage) to about 500 psi (3450 kPa gage); the mole ratio of monoolefin to hydrogen is from about 1:1 to about 1:20; and the contacting time is from about 10 minutes to about 20 hours.

3. A process as claimed in claim 1 wherein the catalyst is a mixture of 50 weight percent of WC and 50 weight percent of $W_2C$.

4. A process as claimed in claim 1 wherein the catalyst is $Mo_2C$.

5. A process as claimed in claim 1 wherein the catalyst is at least one of FeC, MnC, $Mo_2C$, MoN, $MoSi_2$, and a mixture of 50 weight percent of WC and 50 weight percent of $W_2C$.

6. A process as claimed in claim 1 wherein the contacting is carried out in a continuous manner; the temperature in the reaction zone is in the range from about 100° C to about 450° C (212° – 842° F); the pressure is in the range from about 14.7 psi (101 kPa gage) to about 500 psi (3450 kPa gage); the volume ratio of olefin to hydrogen is from about 1:1 to about 1:20; and the space velocity of monoolefins is from about 1 to about 500 volumes feed per volume catalyst per hour (GHSV).

7. A process as claimed in claim 1 wherein the monoolefinic hydrocarbons contain from 2–20 carbon atoms per molecule.

8. A process as claimed in claim 1 wherein the elevated activation temperature is from about 300° C to about 600° C (572° – 1112° F) and the time period for activation is between one and three hours.

9. A process as claimed in claim 1 wherein the olefinic hydrocarbon is an acyclic monoolefin containing from 2 to 12 carbon atoms per molecule.

10. A process as claimed in claim 1 wherein the olefinic hydrocarbon is butene-2.

* * * * *